United States Patent [19]

Johnson et al.

[11] 4,340,732
[45] Jul. 20, 1982

[54] BUTENOLIDE HERBICIDES AND PROCESS FOR THEIR PREPARATION

[76] Inventors: Alan W. Johnson, c/o The School of Molecular Sciences, University of Sussex, Falmer, Brighton, England, BN1 9QJ; Ahmed Hassanali-Walji, P.O. Box 786, Dar-es-Salaam, United Rep. of Tanzania

[21] Appl. No.: 123,257

[22] Filed: Feb. 20, 1980

[51] Int. Cl.³ .................... A01N 43/26; C07D 407/12
[52] U.S. Cl. ........................................ 542/426; 71/88; 542/413
[58] Field of Search ............................... 542/426, 413

[56] References Cited

U.S. PATENT DOCUMENTS 4,002,459  1/1977  Johnson et al. ..................... 71/88

OTHER PUBLICATIONS

Johnson et al., Weed Res. 16, 223-7, (1976).
Kendall, Org. Chem. 44, 1421 (1979).
Cooper et al., J. Org. Chem., vol. 44, 3414-3416 (1979).
Cook et al., Science 154, 1189 (1966).
Cook et al., J. Amer. Chem. Soc. 94, 6198 (1972).
Heather et al., J. Amer. Chem. Soc. 96, 1976 (1974).
MacAlpero et al., J. Chem. Soc., Perkins I, pp. 410-416, (1976).

Primary Examiner—Mark L. Berch
Attorney, Agent, or Firm—Burns, Doane, Swecker & Mathis

[57] ABSTRACT

New butenolide derivatives of the formula

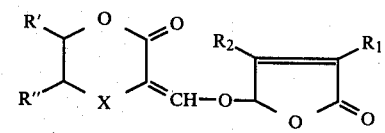

a process for preparing them and herbicidal compositions containing them. These derivatives are useful in the control of parasitic weeds of the genera Striga and Orobanche.

4 Claims, No Drawings

BUTENOLIDE HERBICIDES AND PROCESS FOR THEIR PREPARATION

The present invention relates to novel compounds and to processes for the preparation of such compounds which are useful for the control of certain parasitic weeds. The invention also includes weed control compositions suitable for this purpose. More particularly the invention relates to novel compounds and herbicidal compositions prepared therefrom which are useful for controlling the weeds *Striga hermonthica, Striga asiatica (lutea), Orobanche crenata, Orobanche ramosa* or *Orobanche aegyptiaca* which are parasitic on certain economically important crops such as sorghum, maize, sugar cane and/or broad beans. These compounds and compositions also show some activity against *Alectra vogelli*, a parasite plant which attacks cowpea in certain African territories, especially Tanzania.

It is known that certain compounds and herbicidal compositions containing such compounds, described in British patent specification No. 1,470,097, are useful in the control of parasitic weeds of the genera Striga and Orobanche. Some of these compounds suffer from the disadvantage that they tend to be slightly unstable in the locus where they are intended to be used as herbicides.

The present invention is based on the discovery that related novel compounds possess improved stability or more effective herbicidal activity than the foregoing known compounds and these novel compounds are able to act as effective germination stimulants for the seeds of *Striga hermonthica, Striga asiatica, Orobanche crenate, Orobanche ramosa* or *Orobanche aegyptiaca*. They are also active against *Alectra vogelii*.

According to the invention there is provided a compound of the formula I:

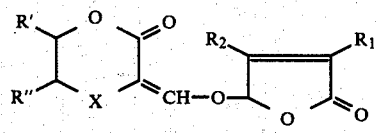

wherein —X— represents a direct single bond or a —CH$_2$— linkage, and wherein when R$_1$ and R$_2$, which may be the same or different, stand for hydrogen, an alkyl radical of one to five carbon atoms or an aryl radical, substituted or unsubstituted, then R' and R" are joined, together with the adjacent two carbon atoms, to form a ring structure of the formula:

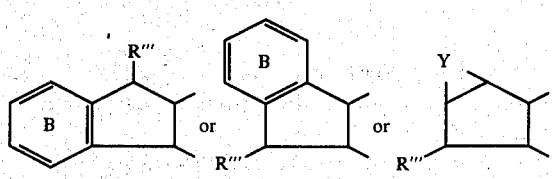

or wherein when R$_1$ and R$_2$ are joined, together with the adjacent two carbon atoms, to form a ring structure of the formula:

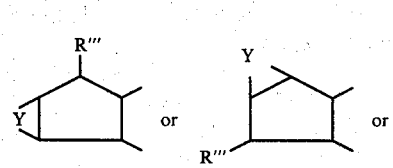

then R' and R", which may be the same or different, stand for hydrogen, an alkyl radical of one to five carbon atoms or an aryl radical, substituted or unsubstituted, or they may be joined, together with the two adjacent carbon atoms, to form a ring structure of the formula:

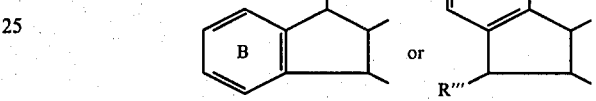

wherein Y represents two hydrogen atoms, an additional bond or an epoxy group; R''' stands for hydrogen, an alkyl radical of one to five carbon atoms or an aryl radical, substituted or unsubstituted and the benzene rings A and B may be substituted by one or more substituents, the same or different, or one or both of the benzene rings A and B may have fused thereto a benzene ring or a heterocyclic ring.

As representative compounds of the invention there may be mentioned compounds corresponding to one of the formulae II, III, IV, V, VI, VII, VIII and IX:

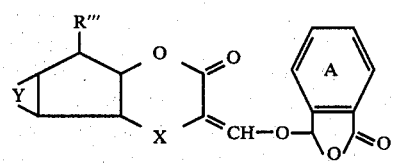

II

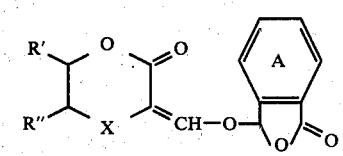

III

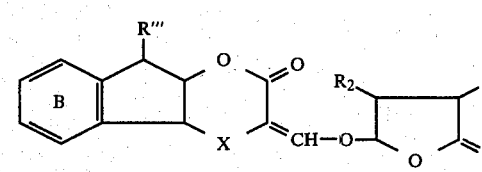

IV

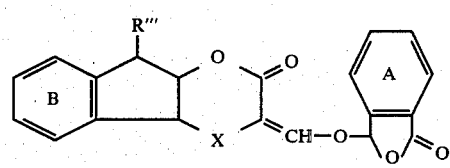

V

-continued

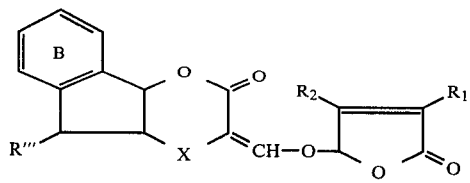 VI

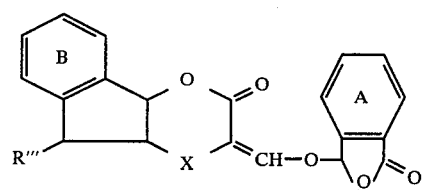 VII

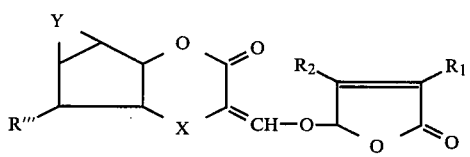 VIII

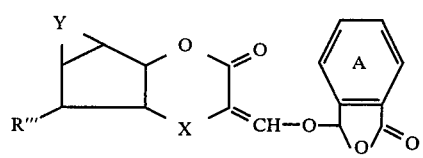 IX wherein R₁, R₂, R', R", R'", X, Y, A and B have the meanings stated above.

As a particular substituent for the alkyl radical R₁, R₂, R', R" or R'" there may be mentioned a methyl, ethyl, n-propyl, isopropyl, n-butyl, sec.-butyl, tert.-butyl or pentyl radical and of these, methyl is preferred. The substituent R₁, R₂, R', R" or R'" may be an aryl radical such as a phenyl or naphthyl radical optionally substituted by one or more alkyl, alkoxy or halogen radicals. The representation —X— is preferably a direct single bond and the representation —Y— is preferably an additional bond. The benzene rings A and B may be substituted by one or more substituents selected from alkyl or alkoxy radicals of one to 8 carbon atoms, such as methyl, ethyl, propyl, butyl, methoxy, ethoxy, propoxy or butoxy, halogen such as chlorine or bromine, aryl, such as phenyl or naphthyl, or aralkyl, such as benzyl. As stated above, one or both of the benzene rings A and B may have fused thereto a benzene ring or a heterocyclic ring whereby the said benzene ring A and/or benzene ring B becomes enlarged to a naphthalene ring or a benzo-heterocyclic ring thus providing a compound of higher molecular weight.

Particularly useful compounds falling within the above stated formula I are compounds represented by formulae IIA, IIIA, IVA, VA, VIA, VIIA, VIIIA, IXA and XA as follows:

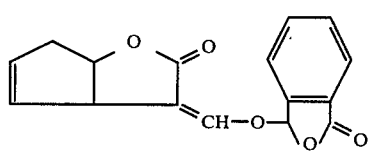 IIA

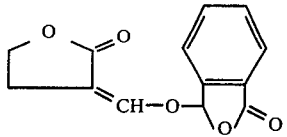 IIIA

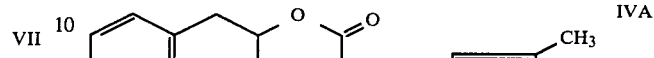 IVA

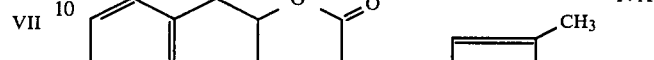 VA

 VIA

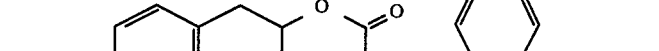 VIIA

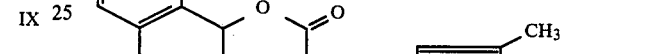 VIIIA

 IXA

 XA

Of the compounds indicated above, those compounds of formulae VIA and VIIIA are particularly preferred compounds.

According to a further feature of the invention there is provided a process for the manufacture of a compound of the above stated formula I which comprises reacting a derivative of an enol compound represented by the formula IA:

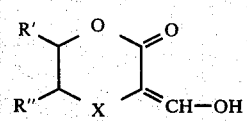 IA with an appropriate butenolide derivative of the formula IB:

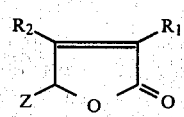 IB wherein $R_1$, $R_2$, R', R" and —X— have the meanings stated above and Z stands for a halogen atom, a methanesulphonate radical ($CH_3SO_2O$—) or a tosylate radical ($CH_3C_6H_4.SO_2O$—).

The said derivative of the enolic form of an α-formylbutenolide is preferably a metallic derivative thereof in the form of a salt of the enol such as an alkali metal salt for example the sodium salt. Suitable salts for use in the preparation of the preferred compounds are the sodio-enolate salt of 3-hydroxymethylene-1,4-butyrolactone, the sodio-enolate salt of the γ-lactone of 4-hydroxycyclopentenyl-5-(α-formylacetic acid), the sodio-enolate salt of the γ-lactone of indan-2-ol-1-(α-formylacetic acid), the sodio-enolate salt of the γ-lactone of indan-1-ol-2(α-formylacetic acid) and the sodio-enolate salt of the γ-lactone of 3-cyclopentenyl-4-(α-formylacetic acid).

A suitable synthesis for the preparation of the enol compound, in the form of its sodium salt, used as starting material for the preparation of compound IVA or VA is as follows:

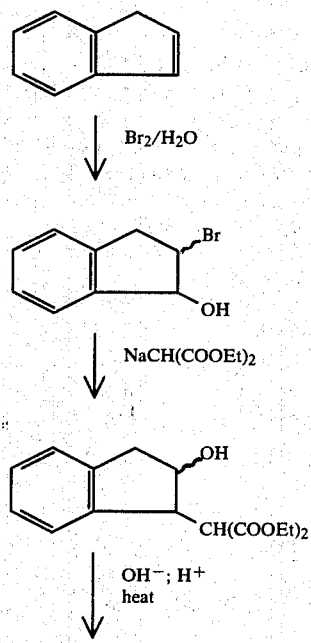

Suitable syntheses for the preparation of the enol compound, in the form of its sodium salt, used as starting material for the preparation of compound VIA, VIIA or XA are as follows:

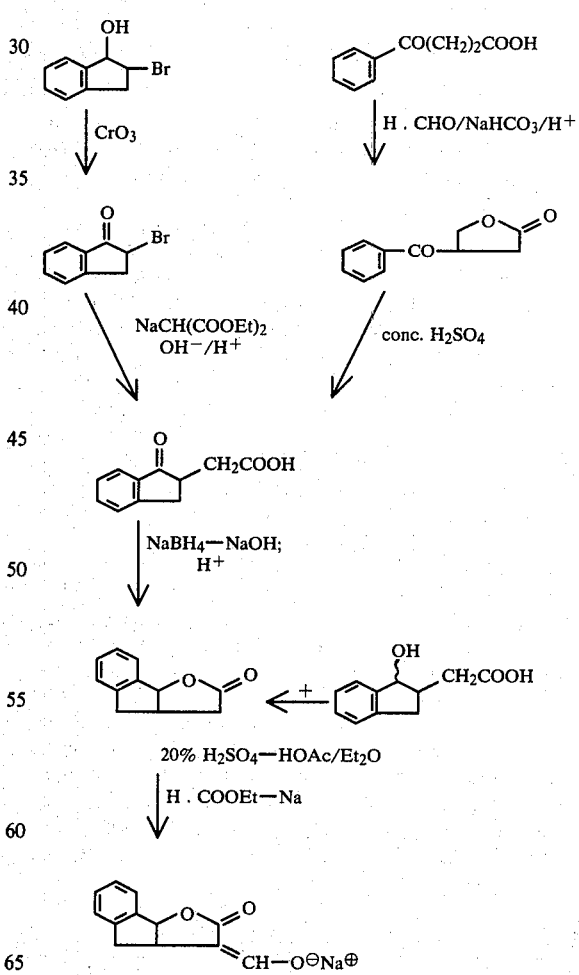

A suitable synthesis for the preparation of the enol compound, in the form of its sodium salt, used as starting material for the preparation of compound VIIIA or IXA is as follows:

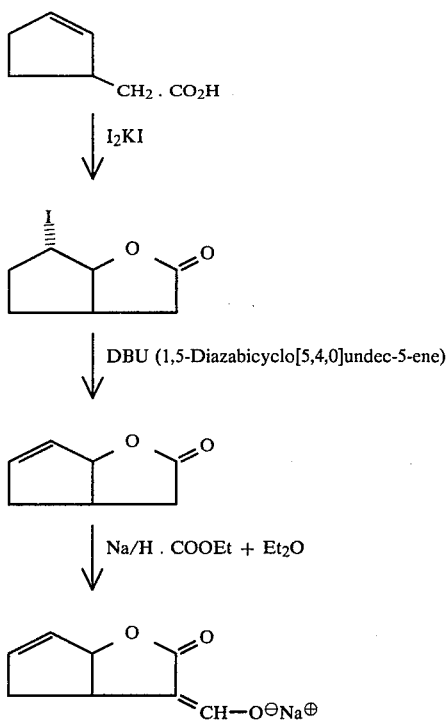

The said butenolide derivative of formula IB, as stated above, may be in the form of the methanesulphonate or a tosylate or in the form of a halogen derivative such as the chloro derivative (Z=Cl) or the bromo derivative (Z=Br). Suitable butenolide derivative for use in preparation of the preferred compounds are 3-bromophthalide, 5-chloro-3-methylbut-2-enolide, 3-methyl-but-2-enolide-5-methanesulphonate, 3-methyl-but-2-enolide-5-p-toluenesulphonate and 5-bromo-4-methylbut-2-enolide.

The said process may be conveniently carried out in the presence of a suitable solvent or diluent such as an organic solvent or diluent for example 1,2-dimethoxyethane. The process conveniently may take place at a temperature over the range of 0° to ambient temperature until reaction is complete and the period of reaction may be of the order of 10 to 20 hours.

The said butenolide derivative of formula IB, may be prepared by known means according to preparative details described in the literature. Alternatively, the compound, 5-chloro-3-methylbutenolide or 5-bromo-3-methylbutenolide, can conveniently be prepared by an improved process which provides 3-methylbutenolide in a single stage process. This important intermediate can now be prepared by heating 3-methyl-γ-butyrolactone with a mixture of bromine and phosphorus to give 3-methylbutenolide which can then be chlorinated or brominated, by known means, to give 5-chloro-3-methylbutenolide or 5-bromo-3-methylbutenolide according to the reaction scheme:

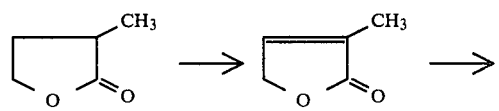

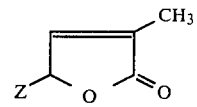

wherein Z stands for chlorine or bromine. This novel preparative route provides the useful intermediate, 3-methylbutenolide, more conveniently and in better yield than by those processes already described in the literature.

Another process leading to the required butenolide derivative of formula IB, for example 5-chloro- or 5-bromo-3-butenolide, involves an alternative improved process for 3-methylbutenolide. The latter can be prepared by reaction of an ester of pyruvic acid, such as ethyl pyruvate, with a vinyl derivative, such as vinyl acetate, in the presence of a titanium salt, such as titanium tetrachloride, and subsequent cyclisation to form a 5-substituted-3-methylbutenolide, for example 5-ethoxy-3-butenolide. The latter can then be converted into 5-chloro- or 5-bromo-3-methylbutenolide by known means, for example by heating with thionyl chloride to provide 5-chloro-3-methylbutenolide as follows:

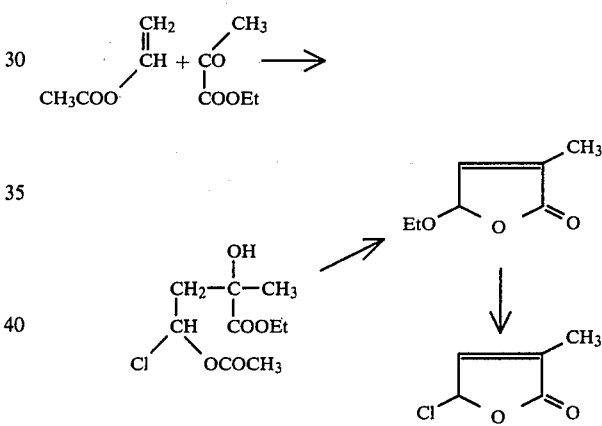

It is to be understood that the compounds of the present invention may exist in different stereoisomeric forms. Each compound has an optically active centre in the right hand ring structure of its formula. In addition, any compound which has more than one ring in the left hand ring structure of its formula has a second chiral feature as illustrated by reference to the structures of compounds IVA and VIIIA wherein the asymmetric centres are shown below:

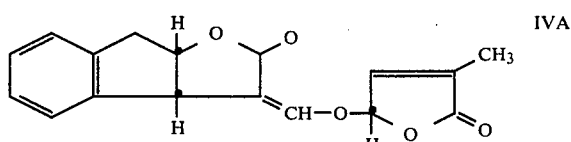

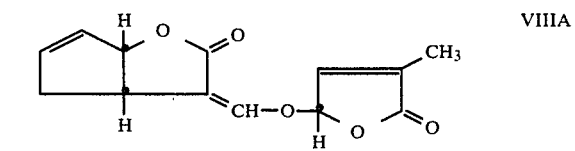

In view of the cis fusion of the rings, each of the said compounds may exist only in two diastereoisomeric forms which can be separated one from another. For example, compound IVA has been separated into its two diastereoisomeric forms, identified conveniently as the "slow" isomer and the "fast" isomer respectively according to the rate at which each isomer is eluted from a silica column (see Example 3 hereinafter). Likewise, compound VIIIA has been separated into its two diastereoisomeric forms identified as the "slow" isomer and the "fast" isomer. Each such diastereoisomeric form of each of these compounds may be further separated into its dextrorotatory (D)-form and its laevorotatory (L)-form.

It is therefore to be further understood that the compounds of the present invention include all possible stereoisomeric forms of each compound.

According to a further feature of the invention, there is provided a method for controlling at least one of the parasitic weeds, *Striga hermonthica*, *Striga asiatica* (*lutea*), *Orobanche crenata*, *Orobanche ramosa* and *Orobanche aegyptiaca* which comprises contacting dormant seeds thereof with a compound corresponding to the formula I, wherein $R_1$, $R_2$, $R'$, $R''$, $R'''$, X, Y, A and B have the meanings stated above.

In carrying out the method for controlling said weeds, it is generally preferred that the host plant, i.e. the plant on which the germinated weed seeds attach themselves and grow, is absent from the soil containing the parasitic weed seeds being treated, or that the host plant has substantially reached maturity so that any infestation of the host plant by the parasitic weed following germination of the seeds thereof will have a minimal effect on the host plant and harvesting of the latter or natural death at the end of the growing season will prevent the parasitic weed from reaching maturity and consequently re-seeding itself. It is however to be understood that the said method may conveniently be carried out at other periods during the life of the host plant. Thus, it may be convenient to carry out the said method using one of the compounds of the present invention in admixture with a selective herbicidal agent after the sowing of the host plant or during the period of active growth of the host plant.

It may also be advantageous to give the seeds of Orobanche or Striga species a preliminary treatment with a solution of gibberellic acid before treatment with one of the compounds of the present invention as a method of controlling these parasitic weeds.

The invention therefore consists of the provision of a herbicidal composition comprising as an active ingredient a compound of the formula I wherein $R_1$, $R_2$, $R'$, $R''$, $R'''$, X, Y, A and B have the meanings stated above, in association with a suitable carrier or diluent therefor.

The compound of formula I is preferably applied to the soil containing the dormant parasitic weed seeds in the form of a composition containing the active compound in admixture with a suitable carrier or diluent. Suitable carriers or diluents are particularly finely divided solid inert carriers or diluents such as powdered chalk, powdered clays, or powdered conventional fertilizers. Also suitable are liquid carriers or diluents such as water or an organic liquid. Pre-mixes of a relatively high concentration of the active agent with a carrier may be formulated for ease of handling, particularly for ease in preparing the final herbicidal composition to be applied to the soil. For instance, such a pre-mix may take the form of a solution of the active compound in an inert organic solvent, such solution optionally containing a surface active agent selected to promote the formation of an aqueous emulsion when the concentrate is diluted with a large volume of water for application to the soil.

The active compound to be used in the above method for controlling weeds or the above herbicidal compositions is preferably a compound of formula II, III, IV, V, VI, VII, VIII or IX. Such a compound may be applied to the soil containing the parasitic weed seeds in amounts of from 100 to 5000 grams/hectare or from 0.01 to 0.5 gram/cubic meter of soil, and for this purpose compositions may be used containing from 0.001 to 1000 parts per million of the active compound, the balance of such compositions being essentially diluent or carrier as described above. Too little of the active compound may secure insufficient germination of the parasitic weed seeds to afford effective control. Naturally, temperature and moisture conditions in the soil should be suitable for the germination of the parasitic weed seed.

A more preferred compound to be used in the method for controlling the said weeds or to be used in the herbicidal compositions is a compound of the formula IIA, IIIA, IVA, VA, VIA, VIIA VIIIA, IXA or XA. Of these, the compounds presently of choice are the compounds of formulae VIA and VIIIA which are particularly effective against *Orobanche crenata* and *Striga hermonthica*.

It is known that a compound of the formula XIA:

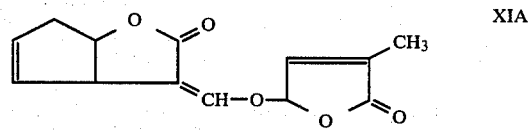

is active as a germination stimulator and may be used as a herbicidal agent in the control of parasitic weeds of the genera Striga and Orobanche. In comparison with the known compound XIA, the preferred compounds VIA and VIIIA of the present invention show an improvement over the said compound XIA as germination stimulators in laboratory tests and it has also been found that a comparable improvement or advantage was obtained when the compounds of the present invention were used as herbicides against Striga and Orobanche weeds.

The invention is illustrated by, but not limited by, the following Examples describing the preparation of compounds of formula I:

EXAMPLE 1

Preparation of Compound IIA

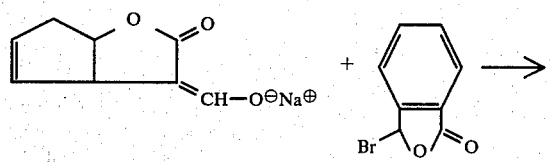

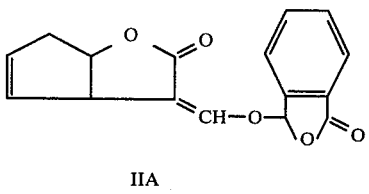

IIA

A mixture of the sodio-enolate salt (0.87 g) and 3-bromophthalide (1.07 g) in anhydrous 1,2-dimethoxyethane (20 ml) was stirred at room temperature for 18 hours and then diluted with ice-cold water (80 ml). The precipitated solid product was collected and recrystallized from a mixture of dichloromethane and hexane. The product, compound IIA, in the form of mixed diastereoisomers, had m.p. 212°–213° (Found: C, 67.6; H, 4.3; $C_{16}H_{12}O_5$ requires C, 67.6; H, 4.25).

EXAMPLE 2

Preparation of Compound IIIA

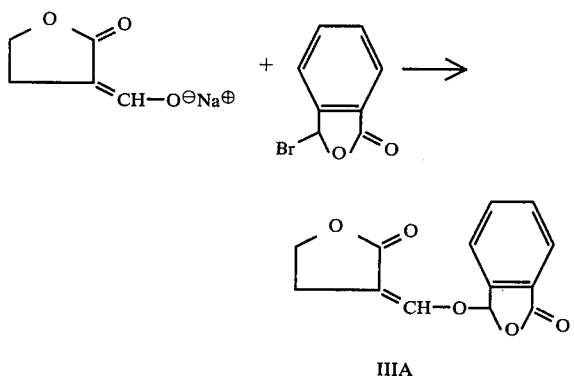

IIIA

3-Bromophthalide (1.07 g) was added to a suspension of the sodio-enolate salt of 3-hydroxymethylene-1,4-butyrolactone (0.68 g) in anhydrous 1,2-dimethoxyethane (15 ml) and the mixture stirred at room temperature for 18 hours. The mixture was then diluted with water (100 ml) and extracted with dichloromethane (3×30 ml). The combined organic extract was washed with water (50 ml) followed by saturated salt solution (50 ml), dried over sodium sulphate and evaporated to dryness. The solid residue crystallized from methylene chloride-hexane mixture to give compound IIIA as colourless needles, m.p. 185°–189°. (Found: C, 63.45; H, 4.15; $C_{13}H_{10}O_5$ requires C, 63.4; H, 4.05).

EXAMPLE 3

Preparation of Compound IVA (i) 2-Bromoindan-1-ol

This was prepared from indene according to the known procedure. The n.m.r. spectrum in deuteriochloroform confirmed that the product was trans-2-bromoindan-1-ol.

(ii) Trans-indan-2-ol-1-acetic acid

This was prepared by modification of the known procedure. Sodium (0.46 g) was added in small pieces to a stirred solution of diethyl malonate (3.2 g) in 1,2-dimethoxyethane (15 ml) at room temperature (3 hours). The resulting solution was treated with a solution of 2-bromoindan-1-ol (2.13 g) in 1,2-dimethoxyethane (12 ml) and the mixture stirred at room temperature overnight. It was then heated under reflux for 1 hour, cooled and evaporated to dryness.

The mixture of crude diester and excess diethylmalonate was saponified by boiling with 2 N sodium hydroxide (60 ml) for 1.5 hours. The resulting solution was cooled, washed with ethyl acetate (30 ml×2), acidified with 6 N hydrochloric acid and saturated with salt. Continuous extraction with ether for 24 hours followed by removal of the solvent gave a solid product which crystallized from benzene-alcohol, when it had m.p. 116°–118°.

The hydroxy-diacid was decarboxylated by heating in an oil bath to about 130° with stirring under an atmosphere of nitrogen for 1 hour. The resulting oil solidified on cooling and was crystallized from benzene-hexane. It had m.p. 124°–132°. (Found: C, 68.6; H, 6.25; $C_{11}H_{12}O_3$ requires C, 68.75; H, 6.25%. The n.m.r. spectrum of the compound clearly showed it to be trans-indan-2-ol-1-acetic acid; double irradiation studies at 220 MHz showed the presence of —$CH_2$—CH—CH—$CH_2$— carbon skeleton, inconsistent with the previous structural assignment.

(iii) Lactonisation of trans-indan-2-ol-1-acetic acid

The hydroxy-acid (2.5 g) (above) was dissolved in 65% concentrated sulphuric acid in acetic acid (10 ml) and kept at room temperature for 24 hours. It was then poured onto cracked ice (300 g) and the aqueous solution extracted with dichloromethane (60 ml×4). The combined organic extract was washed with water (100 ml×2) followed by 5% sodium bicarbonate (50 ml×2) and then saturated salt solution (30 ml). After drying over sodium sulphate, the organic solution was filtered and evaporated to give an oil which slowly crystallized. Recrystallization from dichloromethane-hexane mixture gave the desired lactone as colourless needles, m.p. 73°–74°. (Found: C, 75.85; H, 5.75. $C_{11}H_{10}O_2$ requires C, 75.8; H, 5.7%).

(iv) Formylation of the lactone of indan-2-ol-1-acetic acid

Sodium (0.23 g) was added to a solution of the foregoing lactone (1.74 g) in a mixture of ethyl formate (1.11 g) and ether (20 ml) and the reaction stirred at room temperature for 18 hours. The light-tan sodio-enolate salt was filtered, washed quickly with a small amount of ether and dried overnight in a desiccator.

(v) Reaction of sodio-enolate salt with 5-chloro-3-methylbutenolide

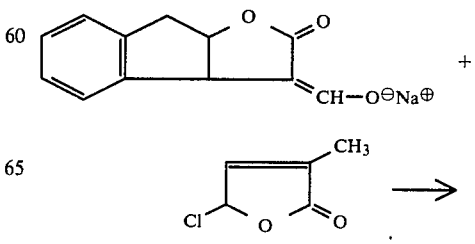

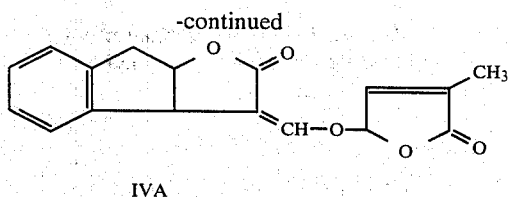

IVA

5-Chloro-3-methylbutenolide (0.66 g) was added to a suspension of the foregoing sodio-enolate salt (1.12 g) in anhydrous 1,2-dimethoxyethane (20 ml) and the mixture stirred for 16 hours. At the end of this period the mixture was diluted with water (50 ml) and extracted with chloroform (60 ml×3). The combined chloroform extract was shaken with saturated salt solution, dried over sodium sulphate, filtered and evaporated to dryness. The residual light brown solid was crystallized from chloroform-ether to give compound IVA as a colourless product (mixed isomers), m.p. 200°–214°. (Found: C, 68.45; H, 4.85; $C_{17}H_{14}O_5$ requires C, 68.45; H, 4.7%). The product, which is a diastereoisomeric mixture, was separated on a silica column (activity III; 84×2.5 cm) eluting with 2% ethyl acetate in ether. The "slow" isomer which had the lower RF value on a silica plate, eluted with ethyl acetate-ether mixtures and had m.p. 205°. The "fast" isomer had m.p. 119°–120°.

The 5-chloro-3-methylbutenolide used as starting material above can be prepared from 3-methyl-γ-butyrolactone by heating with bromine and phosphorus to yield 3-methyl-3-butenolide which can then be converted into 5-chloro-3-methylbutenolide by known means. Alternatively, the 3-methyl-3-butenolide can be converted, if desired, into 5-bromo-3-methylbutenolide, by direct bromination as described in the literature, which can also be used as starting material.

Preparation of 3-methyl-3-butenolide

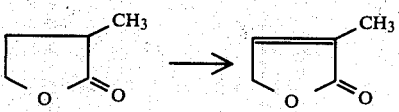

In a 1 liter three-necked round-bottomed flask equipped with a dropping funnel, magnetic stirrer, and an efficient reflux condenser, were introduced 100 g of α-methyl-γ-butyrolactone and 11.6 g of red phosphorus. Over an interval of 30 minutes, 168 g of bromine was added, the mixture being stirred and cooled by an ice bath. The mixture was heated to 70° in an oil bath, and an additional 168 g of bromine was added over an interval of 30 minutes. After the bromine addition, the temperature was raised to 80° and the mixture held at that temperature for 3 hours. Air was then blown into the cooled reaction product until the excess bromine and hydrogen bromide were removed [a trap to catch the resulting vapours is desirable].

The aerated reaction mixture was then heated to 80° on an oil bath and water (20 ml) was added cautiously with stirring. On cessation of the reaction (which takes about 30 minutes), an additional 300 ml of water was added and the mixture was refluxed (using a heating mantle) vigorously for 4 hours. The product was cooled, water (50 ml) was added and then the aqueous layer was saturated with sodium chloride and extracted with methyl chloride (4×100 ml). The combined extracts were dried (sodium sulphate) and the solvent was removed under reduced pressure. The resulting dark-red residue was distilled under reduced pressure to afford 52 g (53%) of 3-methyl-3-butenolide, b.p. 52°/1.5 mm; 82°/7 mm, 97°–98.6°/20 mm.

The 5-chloro-3-methylbutenolide used as starting material can also be prepared conveniently in a three-stage process by reacting ethyl pyruvate with vinyl acetate in the presence of titanium tetrachloride followed by ring closure and subjecting the 5-ethoxy-3-methylbutenolide so obtained to chlorination with thionyl chloride as follows:

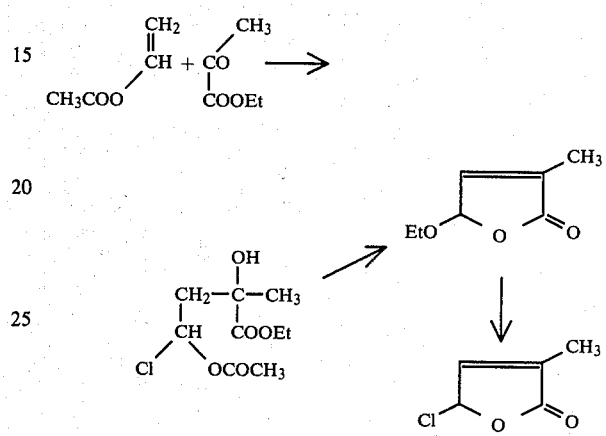

Titanium tetrachloride (8.1 g, 43 m.moles; freshly distilled) in methylene dichloride (60 ml, dried over molecular sieves) was cooled and stirred in an ice bath and then a solution of ethyl pyruvate (4.94 g, 43 m.moles) and vinyl acetate (3.66 g, 43 m.moles) in dry methylene dichloride (30 ml) was added dropwise over 2 hours to the cooled and stirred reaction mixture. Stirring was continued for another 2 hours at 0°. Water (40 ml) was then added, the layers separated and the aqueous layer extracted with further methylene dichloride (2×30 ml). The combined methyl dichloride extract was washed with water (30 ml), dried over sodium sulphate and evaporated to give a colourless oil (7.50 g) which showed n.m.r. ($CDCl_3$) signals at $\delta1.40$ (s, tertiary Me), 6.63 (m) and 2.00 and 2.08 (diastereoisomeric acetates).

The crude colourless oil so obtained (7.12 g) was dissolved in absolute ethanol (80 ml), concentrated hydrochloric acid (4 ml) was added and the mixture heated under reflux for 4 hours. Water (100 ml) was then added, the ethanol was removed by distillation and the remainder heated under reflux for a further 45 minutes. The reaction mixture was then extracted with ethyl acetate (3×50 ml) and the extract dried over sodium sulphate and evaporated. The product was a yellow-brown gum (2.39 g) which showed n.m.r. ($CDCl_3$) signals at $\delta1.90$ (vinyl Me) and 6.00 and 6.38 (2×m, 1 proton each).

The crude yellow-brown gum was heated with thionyl chloride (20 ml) under reflux for 1 hour and then the excess reagent removed by distillation. The residue was distilled under reduced pressure to give a colourless mobile oil (1.4 g) b.p./62°/2 mm. which was identified as 5-chloro-3-methylbutenolide.

EXAMPLE 4

Preparation of Compound VA

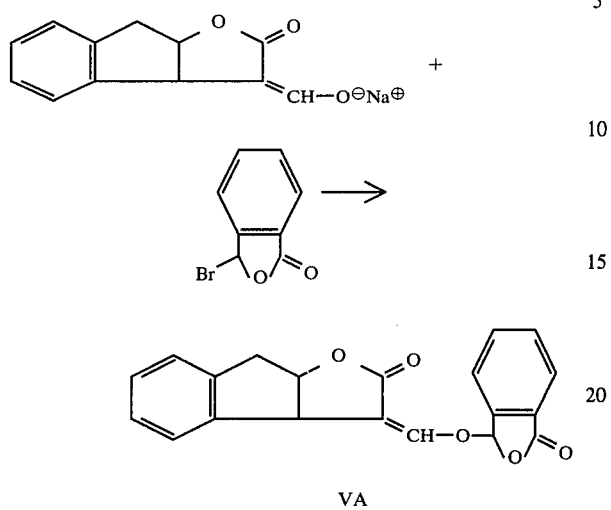

VA

3-Bromophthalide (0.7 g) was added to a suspension of the foregoing sodio-enolate salt (0.75 g), prepared as for compound IVA in Example 3 above, in anhydrous 1,2-dimethoxyethane (15 ml) and the mixture stirred for 18 hours. At the end of this period the mixture was poured into ice (50 g) and the solid product filtered and dried in desiccator. A further crop of the product was obtained by extracting the aqueous mother liquor from above with chloroform (30 ml×3), the extract being dried over sodium sulphate, filtered and evaporated to dryness. Crystallization from dichloromethane-hexane mixture gave compound VA as a crystalline product (mixed diastereoisomers) m.p. 161°–168°. (Found: C, 71.55; H, 4.28. $C_{20}H_{14}O_5$ requires C, 71.85; H, 4.19%).

EXAMPLE 5

Preparation of Compound VIA

Lactonisation of trans-indan-1-ol-2-acetic acid

Trans-indan-1-ol-2-acetic acid (3.4 g) was dissolved in 25% aqueous sulphuric acid (25 ml) and ether (150 ml) was added, the mixture being stirred vigorously at room temperature for 18 hours. The ether layer was separated, shaken with saturated salt solution (25 ml) and dried over sodium sulphate. Filtration and removal of the solvent in vacuo gave an oily product which crystallized on standing. Recrystallization from ether-light petroleum (b.p. 60°–80°) yielded the desired cis-lactone as colourless needles, m.p. 64°–65°.

Formylation of the lactone of cis-indan-1-ol-2-acetic acid

The foregoing cis-lactone (2.61 g) was added to a suspension of sodium (0.345 g) in anhydrous ether (50 ml) followed by ethyl formate (1.8 g) and anhydrous ethanol (1.0 ml). The mixture was stirred at room temperature under nitrogen for 18 hours. The precipitated sodio-enolate salt was filtered, washed quickly with dry ether (25 ml) and dried overnight in a vacuum desiccator.

Reaction of sodio-enolate salt with 5-chloro-3-methylbutenolide

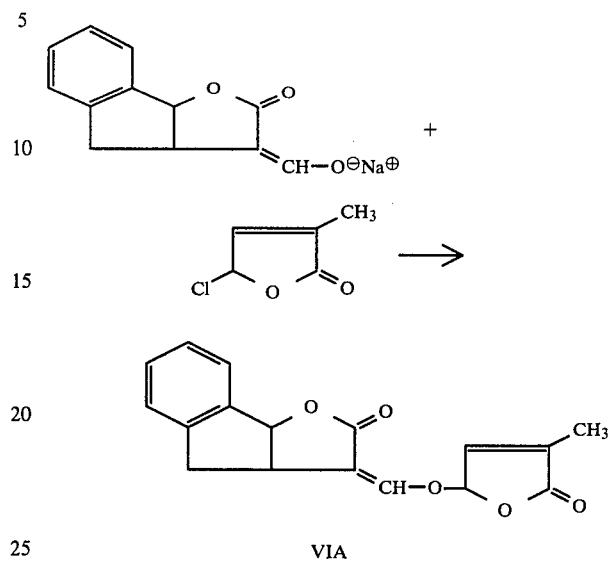

VIA

5-Chloro-3-methylbutenolide (0.663 g) was added to a suspension of the foregoing sodio-enolate salt (1.12 g) in anhydrous 1,2-dimethoxyethane (20 ml) and the mixture stirred for 19 hours. Crushed ice (40 g) was then added and the aqueous solution extracted with chloroform (60 ml×4). The combined chloroform extract was washed with saturated salt solution (20 ml), dried over sodium sulphate, filtered and evaporated to dryness in vacuo. The crystalline solid so obtained was recrystallized from dichloromethane-hexane and gave compound VIA (mixed diastereoisomers) as colourless needles, m.p. 116°–124°. (Found: C, 68.45; H, 4.7. $C_{17}H_{14}O_5$ requires C, 68.45; H, 5.05%).

EXAMPLE 6

Preparation of Compound VIIA

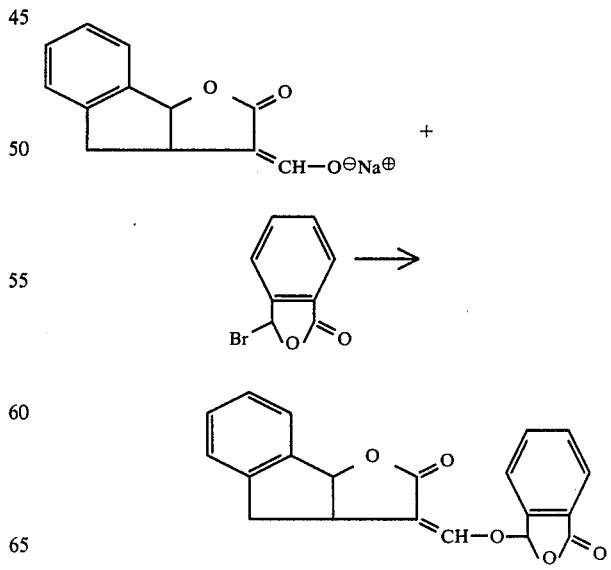

VIIA

A mixture of the sodio-enolate salt (0.75 g), prepared as for compound VIA in Example 5 above, and 3-bromophthalide (0.71 g) in anhydrous 1,2-dimethoxyethane (10 ml) was stirred at room temperature for 19 hours. Ice (20 g) was added and the crystalline solid so obtained was separated and dried. The product was compound VIIA (mixed diastereoisomers) which had m.p. 163°–173°.

EXAMPLE 7

Preparation of Compound VIIIA

Iodolactonisation of Cyclopent-2-enyl-1-acetic acid

A solution of iodine (30 g) and potassium iodide (50 g) in water (200 ml) was added to a mixture of cyclopent-2-enyl-1-acetic acid (12.6g) in 0.5 M sodium bicarbonate (400 ml) and chloroform (300 ml) and the mixture stirred vigorously at room temperature in dark for two days. At the end of this period the chloroform layer was separated, washed with a solution of 10% sodium thiosulphate, followed by a saturated solution of sodium chloride. The resulting chloroform solution was dried over sodium sulphate, filtered and evaporated to dryness to give a thick yellow oil which crystallized on standing. There is thus obtained the desired compound (23.8 g) with the structure

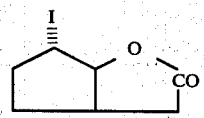

Preparation of Cyclopent-3-ene-2-ol-1-acetic acid lactone

A mixture of the foregoing iodolactone (22.66 g) and 1,5-diazabicyclo[5:4:0]-undec-5-ene (DBU) (13.69 g) in anhydrous tetrahydrofuran (200 ml) was stirred at 50° for 2 hours and heated under reflux for 1½ hours. It was then cooled to room temperature, diluted with water (100 ml) and extracted with dichloromethane (3×60 ml). The combined organic extracts were shaken with saturated salt solution, dried over sodium sulphate, filtered and concentrated to give cyclopent-3-ene-2-ol-1-acetic acid lactone (10.3 g) which was purified by distillation at 69°/0.4 mm. (Found: C, 68.08; H, 6.51, $C_7H_8O_2$ requires C, 67.74; H, 6.45%).

Formylation of the lactone of Cyclopent-3-ene-2-ol-1-acetic acid

Sodium (0.46 g) was added to a solution of the foregoing lactone (2.48 g) in a mixture of ethyl formate (2.22 g) and ether (25 ml) and the reaction stirred at room temperature for 18 hours. The light tan sodium salt was filtered, washed with a small amount of anhydrous ether and dried overnight in a desiccator.

Reaction of sodium salt with 5-chloro-3-methylbutenolide

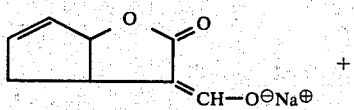

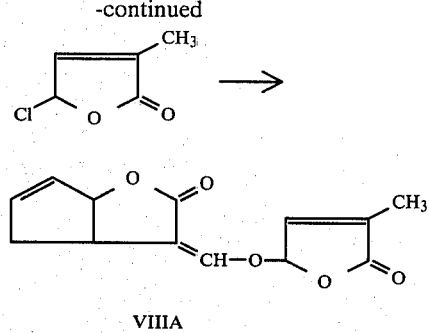

VIIIA

5-Chloro-3-methylbutenolide (1.33 g) was added to a suspension of the foregoing sodium salt (1.74 g) in anhydrous 1,2-dimethoxyethane (20 ml) and the mixture stirred at 5° for 16 hours. It was then diluted with cold water (20 g) and extracted with dichloromethane (3×25 ml). The combined dichloromethane extract was shaken with saturated salt solution, dried over sodium sulphate, filtered and evaporated to dryness to give a viscous oil which solidified on standing. Crystallization from ether gave a colourless crystalline product; m.p. 140°–188° (mixed diastereoisomers) (Found: C, 62.81; H, 4.89. $C_{13}H_{12}O_5$ requires C, 62.90; H, 4.84%) which was identified as compound VIIIA.

EXAMPLE 8

Preparation of Compound IXA

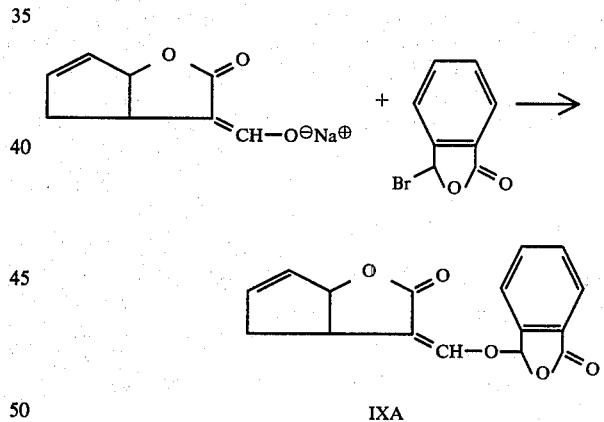

IXA

3-Bromophthalide (1.07 g) was added to a suspension of the sodium salt (0.87 g), prepared as for compound VIIIA in Example 7, in anhydrous 1,2-dimethoxyethane (20 ml) and the mixture stirred at room temperature for 18 hours. It was then diluted with ice-cold water and extracted with dichloromethane (3×25 ml). The combined dichloromethane extract was shaken with saturated salt solution, dried over sodium sulphate, filtered and evaporated to dryness to give a solid (1.45 g) which was crystallized from ether. The product was a colourless crystalline solid, m.p. 178°–200° (dec) (mixed diastereoisomers) (Found: C, 67.47; H, 4.28. $C_{16}H_{12}O_5$ requires C, 67.61; H, 4.23%) which was identified as compound IXA.

EXAMPLE 9

Preparation of compound XA

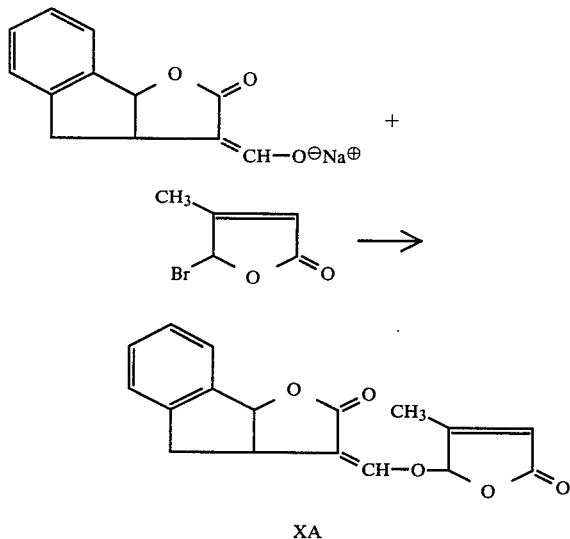

A mixture of the sodio-enolate salt (prepared as for compound VIA in Example 5 but using 4 g of lactone) and 5-bromo-4-methyl-3-butenolide (5 g) in dry tetrahydrofuran (100 ml) was stirred overnight in an atmosphere of nitrogen at room temperature. Most of the solvent was removed under reduced pressure at room temperature and the residue poured into water and extracted several times with methylene chloride. The combined extracts were washed with saturated sodium chloride solution, then aqueous sodium bicarbonate and water. After removal of the solvent from the dried solution, the residue was crystallized from ether-chloroform to give the product as colourless crystals, m.p. 188°–189° which was identified as compound XA. The observed n.m.r. spectrum is in accord with the structure given to compound XA.

In order to demonstrate the activity of the compounds in promoting the germination of seeds of *Striga hermonthica, Striga asiatica, Orobanche aegyptiaca, Orobanche crenata* and *Orobanche ramosa*, the following method was used. Seeds of the parasitic weeds were first sterilized with a 1% aqueous sodium hydrochlorite solution for 10-15 minutes, and then washed with distilled water until free of hypochlorite.

The Striga and Orobanche seeds were pre-treated by incubating at 23° C. under moist conditions, e.g. on moist glass fibre filter paper, for 10-14 days. Usually about 25 seeds on 10 mm discs of the filter paper were employed.

Discs carrying pre-treated seed of Striga or Orobanche were dabbed to remove surplus moisture. Two discs were then placed in each of two replicate dishes, so there were 4 discs per treatment, carrying a total of about 100 seeds. The compounds to be tested were dissolved in ethanol and diluted to the required concentration with distilled water. The amount of ethanol was never greater than 0.5% v/v in the final solution. Freshly prepared solutions were always used. To each disc was added two 16 μl drops of test solution. Dilution of the test solutions by the moisture in the discs was allowed for, so concentrations given were final concentrations. Germination was counted after 2 days at 34° C. in the case of Striga and 5 days at 23° C. in the case of Orobanche.

TABLE 1

Germination tests on *Striga hermonthica*

| Concentration (p.p.m.) | % Germination Compound IIA | Compound IIIA |
|---|---|---|
| 100 | 32 | 33 |
| 50 | 43 | 39 |
| 10 | 35 | 25 |
| 5 | 38 | 17 |
| 1 | 29 | 1 |
| 0.5 | 30 | 6 |
| 0.1 | 0 | 16 |

Control (distilled water): 6% germination

It will be seen that both compounds are active and compound IIA is more active than compound IIIA.

TABLE II

Germination tests on *Orobanche ramosa*

| Concentration (p.p.m.) | % Germination Compound IIA | Compound IIIA | Compound IVA | Compound VA |
|---|---|---|---|---|
| 100 | 0 | 0 | 1 | 1 |
| 10 | 0 | 1 | 2 | 2 |
| 1 | 2 | 0 | 0 | 2 |
| 0.1 | 0 | 0 | 0 | 3 |
| 0.01 | 50 | 42 | 55 | 10 |
| 0.001 | 13 | 34 | 50 | 46 |
| 0.0001 | 30 | 21 | 50 | 9 |

Control (distilled water): 9% germination

It will be seen that all four compounds are active and that compound IVA is the most active compound of the four compounds tested.

TABLE III

Germination tests on *Orobanche crenata*

| Concentration (p.p.m.) | % Germination Compound IVA ("slow" moving isomer) | Compound IVA ("fast" moving isomer) | Compound XIA |
|---|---|---|---|
| 1 | 50 | 66 | 49 |
| 0.1 | 18 | 39 | 14 |
| 0.01 | 9 | 8 | 0 |

Control (distilled water): 0% germination

It will be seen that there is no marked difference between the unresolved DL-pairs of diastereoisomers (the "slow" and "fast" isomers) of compound IVA. Each of these isomers is superior in activity to compound XIA.

TABLE IV

Germination tests on *Orobanche crenata*

| Concentration (p.p.m.) | % Germination Compound VIA | Compound VIIA | Compound XIA |
|---|---|---|---|
| 100 | 27 | 18 | 24 |
| 10 | 37 | 3 | 18 |
| 1 | 42 | 2 | 5 |
| 0.1 | 14 | 5 | 3 |
| 0.01 | 8 | 6 | 1 |
| 0.001 | 3 | 16 | 1 |
| 0.0001 | 1 | 5 | 0 |

Control (distilled water): 1% germination

Each of the compounds VIA and VIIA is superior in activity to compound XIA over the lower range of concentration.

TABLE V

Germination tests on *Striga hermonthica*

| Concentration (p.p.m.) | % Germination | | |
|---|---|---|---|
| | Compound IVA ("slow" moving isomer) | Compound IVA ("fast" moving isomer) | Compound XIA |
| 100 | 9 | 1 | 1 |
| 50 | 17 | 3 | 7 |
| 10 | 10 | 9 | 8 |
| 5 | 50 | 44 | 23 |
| 1 | 60 | 28 | 24 |
| 0.5 | 44 | 10 | 18 |
| 0.1 | 7 | 19 | 12 |
| 0.05 | 8 | 20 | 28 |
| 0.01 | 10 | 22 | 21 |
| Control (distilled water): 2% germination | | | |

Both the "slow" moving isomer and the "fast" moving isomer of compound IVA show appreciable activity. Each of these isomers is superior in activity to compound XIA over certain ranges of concentration.

It has been demonstrated in Hyderabad, during the Kharif (second) rains, that compound VIIIA was effective, at a concentration of 10 p.p.m. and 1 p.p.m., in significantly reducing *Striga asiatica* in a field test on a black soil, being 39% and 36% respectively more efficient than a control treatment. Furthermore, compounds VIA and VIIIA have been shown to be active in germinating *Orobanche ramosa* seeds in vitro, at concentrations of 0.1 to 1.0 p.p.m., having obtained germinations of about 80% to 90% twelve days after treatment. Again, compound VIIIA was shown to be active in stimulating germination of *Orobanche ramosa* seeds carried on glass fibre paper discs and placed on the surface of sterilized sandy loam soil in glass beakers, or when buried 5 cm deep in said soil or when incorporated into said soil. Thus results show that compound VIIIA is as active in sterilized soil as it is in vitro.

What is claimed is:

1. A compound represented by one of the formulae IIA, IIIA, IVA, VA, VIA, VIIA, IXA and XA as follows:

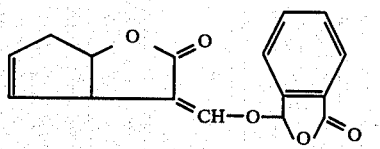
IIA

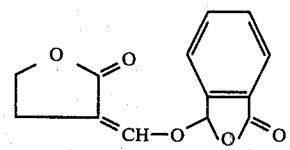
IIIA

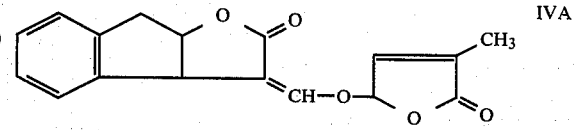
IVA

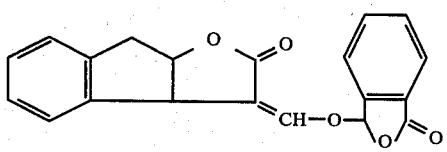
VA

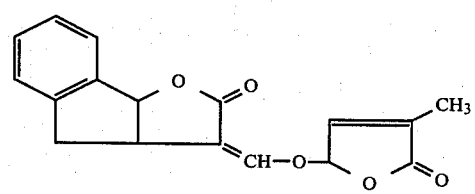
VIA

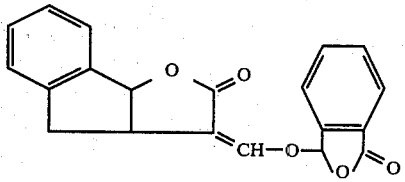
VIIA

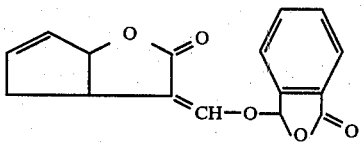
IXA

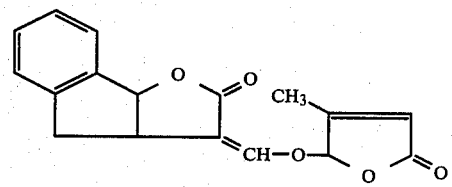
XA

2. A compound as defined in claim 1 and represented by the formula IVA.

3. A compound as defined in claim 1 and represented by the formula VIIA.

4. A compound as defined in claim 1 and represented by the formula VIA.

* * * * *